United States Patent
Erlen

(10) Patent No.: US 11,701,465 B2
(45) Date of Patent: Jul. 18, 2023

(54) SENSOR SYSTEM

(71) Applicant: B. BRAUN MELSUNGEN AG, Melsungen (DE)

(72) Inventor: Christoph Erlen, Kassel (DE)

(73) Assignee: B. Braun Melsungen AG, Melsungen (DE)

( * ) Notice: Subject to any disclaimer, the term of this patent is extended or adjusted under 35 U.S.C. 154(b) by 825 days.

(21) Appl. No.: 16/616,054

(22) PCT Filed: May 22, 2018

(86) PCT No.: PCT/EP2018/063385
§ 371 (c)(1),
(2) Date: Nov. 22, 2019

(87) PCT Pub. No.: WO2018/215465
PCT Pub. Date: Nov. 29, 2018

(65) Prior Publication Data
US 2020/0390972 A1    Dec. 17, 2020

(30) Foreign Application Priority Data

May 23, 2017  (DE) ..................... 10 2017 111 301.0

(51) Int. Cl.
*A61M 5/168*    (2006.01)
*A61M 39/28*    (2006.01)
(Continued)

(52) U.S. Cl.
CPC ...... *A61M 5/16813* (2013.01); *A61M 39/284* (2013.01); *F04B 43/12* (2013.01); *G01B 7/003* (2013.01)

(58) Field of Classification Search
CPC .............. A61M 5/16813; A61M 5/168; A61M 5/14228; A61M 5/16831; A61M 39/284;
(Continued)

(56) References Cited

U.S. PATENT DOCUMENTS

| | | | |
|---|---|---|---|
| 4,460,358 A | 7/1984 | Somerville et al. | |
| 4,504,263 A | 3/1985 | Steuer et al. | |

(Continued)

FOREIGN PATENT DOCUMENTS

| | | |
|---|---|---|
| CN | 102548597 A | 7/2012 |
| DE | 102010043574 A1 | 5/2012 |

(Continued)

OTHER PUBLICATIONS

Office Action received in Russian Application No. 2019142699/14 dated Sep. 3, 2021, with translation, 14 pages.

(Continued)

*Primary Examiner* — Craig J Price
*Assistant Examiner* — Andrew J Rost
(74) *Attorney, Agent, or Firm* — Christopher A. Rothe; Culhane Meadows PLLC

(57) ABSTRACT

A sensor system for a volumetric pump operating according to the linear peristalsis principle includes at least one sensor unit; at least one sensor transmitter unit; and a sensor output signal processing unit. The sensor transmitter unit is arranged to apply a detection variable varying as a function of a travel position to the sensor unit along a predetermined travel along which a fixedly arranged sensor unit and a movably arranged sensor transmitter unit or a movably arranged sensor unit and a fixedly arranged sensor transmitter unit are moving relative to each other. The sensor unit is configured to output a detection signal corresponding to a travel position on the basis of the varying detection variable. The sensor output signal processing unit is arranged to receive the detection signal output by the sensor unit and discriminate at least three travel positions on the basis of the received detection signal.

7 Claims, 1 Drawing Sheet

Figure 1:
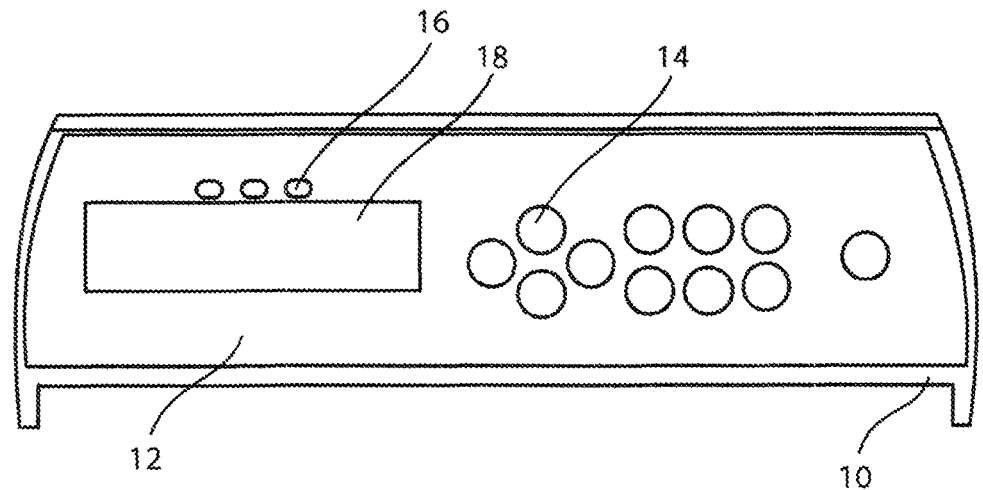

(51) Int. Cl.
*F04B 43/12* (2006.01)
*G01B 7/00* (2006.01)

(58) Field of Classification Search
CPC ...... F04B 43/12; F04B 43/1284; G01B 7/003; G01B 7/023
See application file for complete search history.

(56) References Cited

U.S. PATENT DOCUMENTS

| | | | |
|---|---|---|---|
| 5,219,279 A * | 6/1993 | Natwick | F04B 43/082 92/140 |
| 5,437,635 A * | 8/1995 | Fields | A61M 5/16813 604/153 |
| 5,478,211 A * | 12/1995 | Dominiak | A61M 39/281 607/153 |
| 6,635,033 B1 | 10/2003 | Hill et al. | |
| 8,859,972 B2 | 10/2014 | Cummings et al. | |
| 2004/0177703 A1 | 9/2004 | Schumacher et al. | |
| 2007/0060874 A1 * | 3/2007 | Nesbitt | A61M 5/1408 604/80 |
| 2009/0129944 A1 | 5/2009 | Stemple et al. | |
| 2012/0123322 A1 * | 5/2012 | Scarpaci | A61M 1/28 250/573 |
| 2012/0238991 A1 | 9/2012 | Zhang et al. | |
| 2013/0115120 A1 | 5/2013 | Jarnagin et al. | |
| 2013/0281965 A1 | 10/2013 | Kamen et al. | |
| 2013/0306543 A1 | 11/2013 | Beisser | |
| 2014/0100526 A1 | 4/2014 | Ueda et al. | |
| 2015/0094665 A1 | 4/2015 | Heitmeiter et al. | |
| 2016/0007901 A1 | 1/2016 | Jensen et al. | |
| 2019/0275242 A1 | 9/2019 | Steger et al. | |

FOREIGN PATENT DOCUMENTS

| | | |
|---|---|---|
| DE | 102015117493 A1 | 4/2017 |
| JP | 03205060 A | 9/1991 |
| JP | H11137675 A | 5/1999 |
| JP | 2012249651 A | 12/2012 |
| JP | 2013006021 A | 1/2013 |
| RU | 2323416 C2 | 4/2008 |
| RU | 2612926 C2 | 3/2017 |
| WO | 9310834 A1 | 6/1993 |
| WO | 2007033025 A2 | 3/2007 |
| WO | 2007133942 A2 | 11/2007 |

OTHER PUBLICATIONS

Search Report received in Russian Application No. 2019142699/14 dated Sep. 2, 2021, with translation, 5 pages.
German Search Report for German Application No. 10 2017 111 301.0, with English translation, dated Feb. 7, 2018, 16 pages.
International Search Report and Written Opinion for International Application PCT/EP2018/063385, dated Jul. 19, 2018, 12 pages.
Office Action received in Japanese Application No. 2019-564845 dated Dec. 17, 2021, with translation, 4 pages.
Office Action received in Chinese Application No. 201880039687.6 dated May 18, 2021, with translation, 14 pages.
Search Report received in Chinese Application No. 201880039687.6 dated May 12, 2021, with translation, 5 pages.

* cited by examiner

SENSOR SYSTEM

CROSS-REFERENCE TO RELATED APPLICATIONS

This application is the United States national phase entry of International Application No. PCT/EP2018/063385, filed May 22, 2018, which claims the benefit of priority of German Application No. 10 2017 111 301.0, filed May 23, 2017. The contents of International Application No. PCT/EP2018/063385 and German Application No. 10 2017 111 301.0 are incorporated by reference herein in their entireties.

FIELD

The invention relates to a sensor system for detecting a flap position in a volumetric pump for continuous intravenous administration of infusions.

BACKGROUND

Volumetric pumps (also known as dosing pumps or peristaltic pumps and, resp., Infusomats), such as e.g. an infusion pump, are electric apparatuses for continuous intravenous administration of infusion solutions. There are known, for example, infusion pumps comprising an electronically controlled peristaltic pump at an infusion tube which enable exact dosing of the infusion fluid per time unit.

The conveying principle in pumps of the afore-mentioned type, also referred to as volume-controlled or volumetric pumps, is based on the system of sliding peristalsis by which uniform flow at low pulsation and variable strength can be generated. One wave revolution of the peristalsis corresponds to one working step in which a particular amount of infusion solution is fed to the infusion system by compression of a defined tube volume.

Predominantly, a linear peristalsis is applied in which a tube is pressed to at least one moving peristaltic finger by means of a flap or front flap accessible and operable on the front side of the apparatus, for example. This is intended to suppress uncontrolled flow and the fluid conveyance by the movement of the peristaltic fingers is intended to be controllable. Therefore, the position of the flap is of salient importance to the operation of the apparatus. In a simplified form, a flap may adopt the positions OPEN, SEMI-CLOSED and CLOSED, for example.

The OPEN condition means that the peristalsis is not occlusive, i.e. uncontrolled flow is not suppressed by the peristalsis. The CLOSED condition means that no uncontrolled flow may occur, because at this position of the front flap the latter pinches the tube against the peristalsis and only the movement of the peristalsis controlled by the peristaltic fingers is capable of effectuating flow of a fluid to be conveyed.

Known sensor systems identify the OPEN and CLOSED front flap positions by means of one or more sensors and comprise proximity switches including binary circuit logic most of which are configured to include electromechanical switches and solenoid switches.

While users are familiar with the meanings of the open and, resp., closed conditions of the flap and therefore they can assume a respectively appropriate function of the pump safe for the patient, the SEMICLOSED condition is critical to the patient's safety as in this condition the pump might not be capable of controlling the flow. Therefore, it has to be avoided that users allow the front flap to remain in this condition during operation of the pump and, resp., during actuation thereof.

Previously known sensor systems are not capable of reliably identifying the SEMI-CLOSED flap position so that an apparatus including the known sensor system cannot react to such critical condition.

SUMMARY

Against this background, it is an object underlying the invention to provide a sensor system which identifies the position of a front flap of a volumetric pump in at least an open condition, a semi-closed condition and a closed condition.

This function is intended to be realized with minimum use of hardware and expenditure and with minimum calibrating effort.

Moreover, the sensor system is intended to be capable of outputting alarm, if the front flap remains in a semi-closed condition e.g. longer than a predetermined period of time.

In accordance with the invention, this object is achieved by a sensor system comprising the features of claim 1. Advantageous developments of the invention are the subject matter of the attached subclaims.

According to an underlying inventive idea, a sensor system which is arranged to define and, resp., safely identify at least positions of a flap disposed on the front face (front flap positions) OPEN, SEMI-CLOSED and CLOSED of a front flap of a volumetric pump especially for a medical apparatus, is realized by means of an analogous measuring system defining a rotational position of the front flap and of a flap lever and by means of dynamic evaluation of the measuring signal. Preferably, the front flap is arranged on the front face. Of preference, for this purpose the measuring system includes an analogous sensor, for example a Hall sensor.

Preferably, a front flap of a volumetric pump comprises a manually operable locking lever and a closing mechanism controlled by said locking lever. A SEMI-CLOSED condition, i.e. a semi-closed condition of the flap located between a closed position and an opened position, is a condition in which the flap already engages in the closing mechanism, but the locking lever has not yet been moved completely to an end position and therefore the closing mechanism is not yet completely closed.

In the OPEN position or condition of the flap, the flap is provided outside a predetermined detection range of the analogous sensor so that the flap is not visible to the sensor and the sensor thus provides a zero signal. In the CLOSED position or condition of the flap, the flap is provided closely to the analogous sensor and the flap is visible to the sensor as being located very closely so that the sensor supplies a strong or high signal. The SEMI-CLOSED position in this configuration is evident from the fact that the sensor detects the flap in a position which is approximated to the peristalsis of the pump but is not yet completely in a final position corresponding to the closed position and thus outputs a weak signal which is stronger than the zero signal corresponding to the open condition but is weaker than the strong signal corresponding to the closed position.

The afore-mentioned discriminable signal values or signal levels are preferably realized by an analogous Hall sensor, for example, that is disposed in a main housing of the volumetric pump and a solenoid disposed in the front flap. In such configuration, in the OPEN position of the flap the sensor does not detect the solenoid and, accordingly, will output no signal or a zero signal, in the SEMI-CLOSED position of the flap the sensor detects the solenoid at a remote position and accordingly outputs a weak signal, and in the CLOSED position of the flap the sensor detects the solenoid at a close position and accordingly outputs a strong signal.

Of preference, the detection by the sensor and, resp., the analogous signal is not only connected to the rotational position of the front flap but is additionally also coupled to the position of the locking lever. In this case, only when the flap is closed and the locking lever is provided in its intended final position corresponding to the closed position of the flap, the afore-detected SEMI-CLOSED condition is cancelled, i.e. left, and a condition that is no longer critical is concluded.

In the case of the afore-described pairing of Hall sensor and solenoid, the solenoid may be arranged, for example, on the operating lever or a locking bar mechanically controlled in its position by the flap lever. One design may be such that the analogous sensor signal changes e.g. from strong with an open flap to weak with a semi-closed flap and to strong with a completely closed flap.

Furthermore, a time behavior of the analogous signal may be used for plausibility check or backing of the signal evaluation. For example, the sensor may be arranged to evaluate, on the basis of time behavior, the position of the flap based on adjustment of the signal dynamics to a model of the time behavior. In this case, evaluation by means of thresholds to be calibrated may be advantageously omitted.

As afore-described, by means of the sensor system according to the invention at least three flap positions OPEN, SEMI-CLOSED and CLOSED are identifiable and detectable. Due to the analogous design, advantageously merely one single sensor is required for identifying said at least three conditions. Alternatively, a solution using binary sensors is imaginable, in which case at least two sensors have to be arranged for the discrimination of SEMI-CLOSED and CLOSED. The evaluation of the dynamic time behavior advantageously enables renouncing the calibration and thus enables calibration efforts to be significantly reduced. The evaluation of the dynamic time behavior further advantageously enables a plausibility check of the sensor signals and, with respect to safety aspects, monitoring of the correct sensor function.

According to the invention, the object is achieved in detail by a sensor system for a volumetric pump operating according to the principle of linear peristalsis, comprising at least one sensor unit; at least one sensor transmitter unit; and a sensor output signal processing unit, wherein the sensor transmitter unit is arranged to apply a detection variable varying as a function of a travel position to the sensor unit along a predetermined travel along which a fixedly arranged sensor unit and a movably arranged sensor transmitter unit or a movably arranged sensor unit and a fixedly arranged sensor transmitter unit are moving relative to each other; wherein the sensor unit is configured to output a detection signal corresponding to a respective travel position based on the varying detection variable; and wherein the sensor output signal processing unit is arranged to receive the detection signal output by the sensor unit and to discriminate at least three travel positions based on the received detection signal. In this way, a position of a flap of an infusion pump in which occlusion of the inserted tube is not secured can advantageously be detected.

Preferably, the at least three travel positions include a closed position in which a tube portion inserted in the pump is occluded, an open position in which the tube inserted in the pump is not occluded and an intermediate position provided between the closed position and the open position. Advantageously, in this way a position of a flap of an infusion pump at an intermediate position in which occlusion of the inserted tube is not secured can be detected between the regularly closed condition and the regularly open condition of the flap.

Preferably, the sensor unit is arranged in a housing of the pump and the sensor transmitter unit is arranged at a travel position changing unit adjustably articulated to the housing, or the sensor unit is arranged on a travel position changing unit adjustably articulated to the housing and the sensor transmitter unit is arranged in a housing of the pump. Advantageously, various degrees of freedom for the arrangement of a sensor as sensor unit and of a transmitter element as sensor transmitter unit as well as for the selection of a component part of the pump-flap arrangement ensuring relative movement between the former and thus ensuring a detection signal varying depending on the position and, resp., the travel are provided in this way. Degrees of freedom of said type will be specified in detail in the following aspects.

Of preference, the travel position changing unit is a flap unit of the pump which is configured as a closing device and is arranged to occlude a tube portion inserted in the pump in a closed condition against a peristaltic element disposed in the pump and conveying fluid in the tube portion and to be non-occlusive against the same in an opened position, or the travel position changing unit is a hinge unit on the flap device for articulating the flap device to the housing in an adjustable or foldable manner, or the travel position changing means is a locking bar movably coupled to the flap device of the pump, or the travel position changing unit is a locking lever coupled to the flap device and/or to the housing of the pump.

For example, a sensor may be arranged in the pump and a sensor counter-piece (e.g. solenoid) may be arranged in the flap device configured, e.g., in the form of a front flap, a sensor may be arranged in the front flap and a sensor counter-piece may be arranged in the pump, a sensor may be arranged in a front flap hinge and a sensor counter-piece may be arranged in the pump, a sensor may be arranged in a movable locking bar and a sensor counter-piece may be arranged in the pump, a sensor may be arranged in a locking lever and a sensor counter-piece may be arranged in the pump, a sensor counter-piece (e.g. solenoid) may be arranged on a locking bar and a sensor may be arranged in the pump, a sensor counter-piece (e.g. solenoid) may be arranged on a locking lever and a sensor may be arranged in the pump, and/or a sensor counter-piece (e.g. solenoid) may be fixedly arranged on a front flap and a sensor may be arranged in the pump.

Of preference, the detection signal of the sensor unit is coupled to a rotational position of the flap device forming a first travel position and to a position of the locking lever forming a second travel position, and the sensor output signal processing unit is configured so that an afore-detected condition of an intermediate position is cancelled only when the first travel position indicates that the front flap is completely closed and the second travel position indicates that the locking lever is provided in an intended final position corresponding to the closed position of the flap device.

Of preference, the sensor unit is a Hall sensor and the sensor transmitter unit is a solenoid acting on the Hall sensor, or the sensor unit is a capacitive sensor and the sensor transmitter unit is arranged to bring about a change of capacity corresponding to a covered travel distance of the closing device, or the sensor unit is an inductive sensor and the sensor transmitter unit is arranged to bring about a change of a magnetic field corresponding to a covered travel distance of the closing device in the sensor unit, or the sensor unit is an optical sensor and the sensor transmitter unit is arranged to bring about a change of light incidence corresponding to a covered travel distance of the closing device at the sensor unit, or the sensor unit is an variable resistance-type element, preferably of the type of a potentiometer, and the sensor transmitter unit is arranged to bring about a change of resistance corresponding to a covered travel distance of the closing device at the sensor unit.

For example, advantageously there can be provided a configuration by means of analogous Hall sensors, a configuration by means of capacitive or inductive sensors, a configuration by means of optical sensors and/or a configuration by means of variable resistance-type components such as e.g. a potentiometer and the like.

Of preference, the sensor unit does not detect in a first travel position corresponding to a non-occluded open condition the presence of the sensor transmitter unit and outputs a zero signal as a first detection signal to the sensor output signal processing unit; the sensor unit detects in a third travel position corresponding to an occluded closed condition a near presence of the sensor transmitter unit by way of strong application by the detection variable and outputs a strong sensor signal corresponding to the strong application as a third detection signal to the sensor output signal processing unit; and the sensor unit detects in a second travel position corresponding to an intermediate condition between the occluded closed condition and the non-occluded open condition a remote presence of the sensor transmitter unit by way of an application weaker than the strong application but lying above the zero signal by the detection variable and outputs a sensor output signal weaker corresponding to the weaker application as a second detection signal to the sensor output signal processing unit.

Of preference, the sensor output signal processing unit is arranged to dynamically evaluate the first, second and/or third detection signal along the predetermined travel as analogous signals.

Of preference, the sensor output signal processing unit is arranged to perform a plausibility check of the detection signal based on time behavior of the detection signal.

Of preference, the sensor output signal processing unit is configured to evaluate the travel position by adjusting the dynamics of the detection signal to a model of the time behavior.

Of preference, the sensor output signal processing unit is configured to output an alarm signal when the intermediate position provided between the closed position and the open position is detected longer than a predetermined period of time.

The units, structures, configurations and/or components constituting the sensor system described here may be configured to provide a plurality of modifications including more or less pre-installed configurations and/or separate parts that are to be provided at an appropriate position and are connected or joined during use/in operation.

BRIEF DESCRIPTION OF THE DRAWING FIGURES

Figure 2:
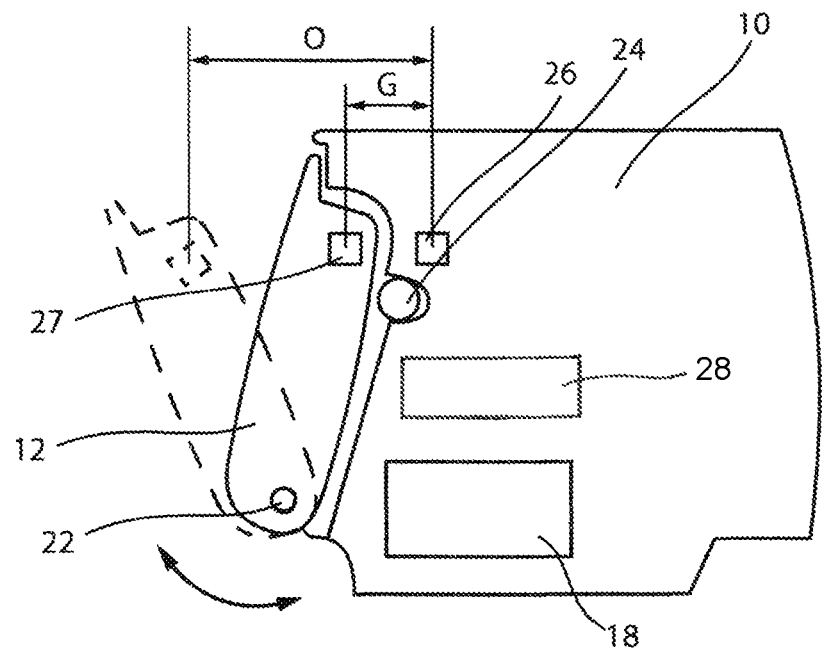

Hereinafter the invention shall be described in detail with reference to the enclosed drawing shown schematically and in simplified form, wherein:

FIG. 1 shows a front view of a volumetric pump, for example of an infusion pump, comprising a sensor system according to an embodiment; and FIG. 2 shows a side view of the volumetric pump according to FIG. 1.

DETAILED DESCRIPTION

Similar or like parts shown in the drawing may be denoted with like reference numerals or may not be denoted with reference numerals, and details thereof will not be redundantly described or explained. Moreover, portions and/or components having no immediate significance to the description of the invention may be omitted or concealed throughout the drawing so as to ensure improved visibility of more important parts.

In the end or front view of the volumetric pump shown in FIG. 1 comprising a sensor system according to an embodiment, in a housing 10 of the pump the functional units, parts and components required for the basic operation of the pump are accommodated. They are known per se and therefore are not redundantly described here.

An end or front side flap (front flap) 12 is articulated to the housing 10 to be foldable. The flap 12 preferably extends over substantially the entire width of the pump housing, as it is one of its functions to open an access for inserting a tube or tube portion transporting fluid, for example an infusion solution, into the pump by appropriately folding up or away. On the outside of the flap, operating elements 14 (indicated by circles, only one thereof being denoted with a reference numeral), at least of an operating condition signaling display 16 (indicated by rounded rectangles, only one thereof being denoted with a reference numeral) that are provided as lamps, for example, and a display device 18 that may be in the form of a liquid-crystal display, for example, are arranged for program run and user communication, for example.

FIG. 2 illustrates a side view of the volumetric pump shown in FIG. 1. The flap 12 is foldable or pivoted on a joint or hinge unit 22 (front flap hinge) in the lower portion of the housing 10 about an axis extending in the longitudinal direction of the housing 10 vis-à-vis the housing 10 along a predetermined travel distance.

The flap 12 may adopt a number of travel positions along the predetermined travel.

A first position or travel position is a closing position or closed position in which the flap 12 is guided closely to the housing 10 and ensures a tube or tube portion 24 inserted in the pump in e.g. tube guiding portions and/or tube seats to press against a peristalsis (peristaltic finger, peristaltic element) not shown and occludes the tube 24.

A second position or travel position is an open position in which the flap 12 is folded away from the housing (shown in FIG. 2 in broken lines) and releases the access to the pump. An inserted tube 24 is not occluded in the open position of the flap 12.

A third position or travel position is an intermediate position between the closed position or first travel position and the open position. Since an occluding force transmitted by the flap 12 usually is generated and maintained, at least assisted, however, by e.g. a movable locking bar and/or a locking lever (both of which are not shown), an incomplete occlusion of the tube 24 may occur when the locking bar and/or the locking lever is/are provided at an intermediate position and not at a predetermined end position.

In other words, a user may close the flap 12 and actuate the locking bar or the locking lever, respectively. If this is unnoticed performed incompletely, the flap 12 may nevertheless remain at an intermediate position (here also referred to as a semi-closed condition and corresponding to such condition) and may not sufficiently occlude, although the user assumes that a proper closing operation was carried out.

While users are familiar with the meanings of the open and, resp., closed conditions of the flap and, therefore, they can assume an appropriate function of the pump in each case which is safe for the patient, the semi-closed condition is critical to the safety of the patient as the pump in this condition cannot safely control the flow conveyed through the tube or tube portion 24. Therefore, the users must not leave the flap 12 in such condition during operation of the pump and, resp., during actuation thereof.

For detecting an intermediate condition as afore-described, i.e. a position of the flap 12 between the open position and the closed position, according to the present embodiment at least one sensor 26 (sensor unit) and at least one transmitter element 27 applying a detection variable to the sensor (sensor transmitter unit) are arranged in the housing and in the flap 12 to be associated with each other such that, in conformity with the distance between the sensor 16 and the transmitter element 18, at least the closed condition, the open condition and an intermediate position between the closed condition and the open condition, i.e. the first, second and third travel positions of the flap 12, can be detected to be discriminable from each other.

In detail, the sensor system according to the embodiment comprises the at least one sensor 26, the at least one transmitter element 27 and further e.g. a microcontroller or microprocessor 28 including appropriate storage capacity and periphery (sensor output signal processing unit), which is/are known per se and therefore is/are not redundantly described. The sensor 26 may be fixedly arranged in the housing 10 and the transmitter element 27 may be arranged in the flap 12 to be movable with the latter, as shown in FIG. 2. As an alternative, the transmitter element 27 may be fixedly arranged in the housing 10 and the sensor 26 may be arranged in the flap 12 to be movable with the latter.

Basically, there is no particular limitation as regards the arranging position of the sensor 26 and the transmitter element 27 as long as the transmitter element 27 to the sensor 26 may move relative to each other along a predetermined travel along which a fixedly arranged sensor 26 and a movably arranged transmitter element 27 or a movably arranged sensor 26 and a fixedly arranged transmitter element 27 and may apply a detection variable varying as a function of the travel position, i.e. the first, second and third travel positions as afore-described.

In such case the sensor 26 may output, on the basis of the detection variable varying as a function of the travel, a detection signal corresponding to a particular travel position, which is analogous in the present embodiment, to the microcontroller or microprocessor 28.

The microcontroller or microprocessor 28 then is arranged to receive and evaluate the detection signal output by the sensor 26 and as a result to define at least three travel positions, i.e. the first, second and third travel positions, indicating the respective closed position at which a tube or tube portion 24 inserted in the pump is occluded, the respective open position at which the tube or tube portion 24 inserted in the pump is not occluded and the respective intermediate position between the closed position and the open position.

It is noted that although the intermediate position basically may be any position between the open position and the closed position, usefully out of such range of possible intermediate positions at least one predetermined intermediate position from which a closed condition is not detected anymore and/or an open condition is not yet detected is selected to form a threshold by means of e.g. threshold consideration (comparison). Since, in the present embodiment, detection is performed using an analogous signal, corresponding thresholds can be optionally determined, and the microcontroller or microprocessor 28 may be designed to process and detect an optional number of intermediate positions.

When the microcontroller or microprocessor 28 detects an intermediate position that is predetermined between the closed position and the open position, it may be configured to output an alarm signal via e.g. the operating condition signaling display 16, the display unit 18 and/or an acoustic signal from a loudspeaker (not shown) so as to inform the user about said condition, and/or to appropriately restrict, for example stop, the operation of the pump. The alarm signal may be output in a delayed manner, for example not before the intermediate position has been detected for more than a predetermined period of time.

In the afore-mentioned context, the flap 12 thus foul's a travel position changing device adjustably articulated to the housing 10 and simultaneously a closing device which occludes a tube or tube portion 24 inserted in the pump in the closed condition against the peristaltic element disposed in the pump and conveying fluid such as an infusion solution in the tube or tube portion 24 and which is not occlusive against the peristaltic element in the opened condition.

In respective alternative embodiments, the travel position changing device may be the hinge 22 of the flap 12, a locking bar movably coupled to the flap 12 of the pump or a locking lever coupled to the flap 12 and/or the housing 10 of the pump.

For example, the sensor 26 may be arranged in the pump and the transmitter element 27 as a sensor counter-piece, such as a solenoid, may be arranged in the flap 12, the sensor 26 may be arranged in the flap 12 and the transmitter element 27 may be arranged in the pump, the sensor 26 may be arranged in the hinge 22 of the flap 12 and the transmitter element 27 may be arranged in the pump, the sensor 26 may be arranged in the movable locking bar and the transmitter element 27 may be arranged in the pump, the sensor 26 may be arranged in the locking lever and the transmitter element 27 may be arranged in the pump, the transmitter element 27 as a sensor counter-piece, such as a solenoid, may be arranged at the locking bar and the sensor 26 may be arranged in the pump, and/or the transmitter element 27 as a sensor counter-piece, such as a solenoid, may be fixedly arranged at the flap 12 and the sensor 26 may be arranged in the pump.

Advantageously, the detection signals of the sensor 26 may further be coupled both to a position of the flap 12 forming as a first travel position a flap travel position and to a position of the locking lever forming as a second travel position a locking lever travel position. In this case, the microcontroller or microprocessor 28 may be configured to determine that an afore-detected condition of an intermediate position is cancelled only when the flap travel position indicates that the flap 12 is closed in a predefined manner and the locking lever travel position indicates that the locking lever is provided in an intended end position corresponding e.g. to the closed position of the flap 12.

The sensor 26 may be a Hall sensor and the transmitter element 27 may be a solenoid acting on the Hall sensor. In respective alternative embodiments, the sensor 26 may be a capacitive sensor and the transmitter element 27 may apply a change of capacity corresponding to a covered travel distance of the flap 12 to the sensor 26, or the sensor 26 may be an inductive sensor and the transmitter element 27 may apply a change of magnetic field corresponding to a covered travel distance of the flap 12 to the sensor 26, or the sensor 26 may be an optical sensor and the transmitter element 27 may cause a change of light incidence or of an amount of incident light corresponding to a covered travel distance of the closing device, or the sensor 26 may be a variable-resistance element, preferably of the type of a potentiometer, and the transmitter element 27 may initiate a change of resistance corresponding to a covered travel distance of the closing device to the sensor 26.

The sensor system in the present embodiment makes use of analogous signals, for example from Hall sensors, capacitive or inductive sensors, optical sensors and/or variable-resistance components such as e.g. a potentiometer and the like.

However, the application is not limited hereto. The sensor system can be equally realized on the basis of sensors supplying binary signals. In such case, the minimum number of sensors to be arranged is increased corresponding to the travel positions to be discriminated. In the case of three travel positions to be discriminated on a binary basis, then for example at least two sensors 26 outputting binary signals have to be provided.

In the present embodiment, the individual travel positions are detected as described hereinafter. In or at a first travel position of the flap 12 corresponding to the non-occluded open condition (distance 0 between the sensor 26 and the transmitter element 27 in FIG. 2), the sensor 26 does not perceive or detect the presence of the transmitter element 27 and thus outputs a zero signal as a first detection signal to the microcontroller or microcomputer 28. At a third travel position of the flap 12 corresponding to the occluded closed condition (travel G between the sensor 26 and the transmitter element 27 in FIG. 2), the sensor 26 perceives or detects the transmitter element 27 at a short distance or closely ahead of itself due to the detection variable strongly acting on the sensor, and therefore outputs a strong sensor output signal corresponding to the strong application as a third detection signal to the microcontroller or microcomputer 28. At a second travel position corresponding to an intermediate condition between the occluded closed condition and the non-occluded open condition, the sensor 26 perceives or detects the transmitter element 27 more remotely than at the third travel position due to the detection variable acting on the sensor in a way weaker than the strong application at the third travel position but with an intensity above the zero signal and outputs a sensor output signal weaker, corresponding to the weaker application, than a second detection signal to the microcontroller or microcomputer 28.

The first, second and/or third detection signals then can be dynamically evaluated as analogous signals by the microcontroller or microcomputer 28 along the predetermined travel of the flap 12. For example, the microcontroller or microcomputer 28 can perform a plausibility check of the detection signal based on time behavior of one or all of the detection signals so as to monitor the sensor system for correct and safe operation. The travel position may be evaluated, for example, by adjusting the dynamics of the detection signal to a model of the time behavior.

Although particular variables such as weight, absolute length, width and thickness, coloring, shape and insignificant details are not shown, for those skilled in the art such specifications are evidently within the scope of the afore-described embodiment and invention. Moreover, it is understood that the concrete text, a sequence and a content of configurations and components shown in the drawing and described herein are merely illustrating and exemplary and that the apparatus and the operating procedure thereof are not limited thereto.

Therefore and, as is understood, the invention is not limited to the described preferred embodiment and the modifications thereof, and combinations of at least parts of the embodiment, modifications and equivalents are obviously resulting to those skilled in the art as being completely covered by the scope defined by the attached claims.

The invention claimed is:

1. A sensor system with contactless sensors for a volumetric pump operating according to the linear peristalsis principle, which detects the position of a front flap relative to a housing of the volumetric pump, comprising:
   at least one sensor unit;
   at least one sensor transmitter unit; and
   a sensor output signal processing unit, wherein:
   the sensor transmitter unit is arranged to apply a detection variable varying as a function of a travel position to the sensor unit along a predetermined travel along which a fixedly arranged sensor unit mounted on the housing and a movably arranged sensor transmitter unit mounted on the front flap or a movably arranged sensor unit mounted on the front flap and a fixedly arranged sensor transmitter unit mounted on the housing are moving relative to each other,
   the sensor unit is configured to output a detection signal corresponding to a particular travel position of the front flap on the basis of the varying detection variable,
   the sensor output signal processing unit is arranged to receive the detection signal output by the sensor unit and to discriminate at least three travel positions of the front flap on the basis of the received detection signal,
   the at least three travel positions comprise a closed position in which a tube portion inserted in the pump is occluded, an open position in which the tube portion inserted in the pump is not occluded and an intermediate position provided between the closed position and the open position,
   the sensor output signal processing unit is arranged to perform a plausibility check of the detection signal based on time behavior of the detection signal, and
   the sensor output signal processing unit is configured to evaluate the travel position by adjusting the dynamics of the detection signal to a model of the time behavior.

2. The sensor system according to claim 1, wherein
   the sensor unit is disposed in the housing of the pump and the sensor transmitter unit is disposed on a travel position changing unit adjustably articulated to the housing, or
   the sensor unit is disposed on a travel position changing unit adjustably articulated to the housing and the sensor transmitter unit is disposed in the housing of the pump.

3. The sensor system according to claim 2, wherein
   the travel position changing unit is a flap unit of the pump which is configured as a closing device and is arranged to occlude the tube portion inserted in the pump in a closed condition against a peristaltic element disposed in the pump and conveying fluid in the tube portion and to be non-occlusive against the same in an opened condition, or
   the travel position changing unit constitutes a hinge unit disposed on the flap unit which adjustably articulates the flap unit to the housing.

4. The sensor system according to claim 1, wherein
the sensor unit is a Hall sensor and the sensor transmitter unit is a solenoid acting on the Hall sensor, or
the sensor unit is a capacitive sensor and the sensor transmitter unit is arranged to bring about a change of capacity corresponding to a covered travel distance of the closing device in the sensor unit, or
the sensor unit is an inductive sensor and the sensor transmitter unit is arranged to bring about a change of magnetic field corresponding to a covered travel distance of the closing device in the sensor unit, or
the sensor unit is an optical sensor and the sensor transmitter unit is arranged to bring about a change of light incidence corresponding to a covered travel distance of the closing device at the sensor unit, or
the sensor unit is a variable-resistance element, and the sensor transmitter unit is arranged to bring about a change of resistance corresponding to a covered travel distance of the closing device.

5. The sensor system according to claim 1, wherein
in a first travel position corresponding to a non-occluded open condition, the sensor unit does not detect the presence of the sensor transmitter unit and outputs a zero signal as a first detection signal to the sensor output signal processing unit;
in a third travel position corresponding to an occluded closed condition, the sensor unit detects close presence of the sensor transmitter unit by way of a strong application by the detection variable and outputs a sensor output signal corresponding to the strong application as a third detection signal to the sensor output signal processing unit; and
in a second travel position corresponding to an intermediate condition between the occluded closed condition and the non-occluded open condition, the sensor unit detects a remote presence of the sensor transmitter unit by way of an application by the detection variable which is weaker than the strong application but is above the zero signal and outputs a sensor output signal weaker corresponding to the weaker application as a second detection signal to the sensor output signal processing unit.

6. The sensor system according to claim 5, wherein the sensor output signal processing unit is arranged to dynamically evaluate at least one of the first, second or third detection signals as analogous signals along the predetermined travel.

7. The sensor system according to claim 1, wherein the sensor output signal processing unit is configured to output an alarm signal when the intermediate position provided between the closed position and the open position is detected to be longer than a predetermined period of time.

* * * * *